United States Patent
Park (10) Patent No.: US 9,833,269 B2
(45) Date of Patent: Dec. 5, 2017

(54) FIXATOR FOR BAR OF PECTUS EXCAVATUM REPAIR OPERATION

(76) Inventor: Hyung Joo Park, Seoul (KR)

( * ) Notice: Subject to any disclaimer, the term of this patent is extended or adjusted under 35 U.S.C. 154(b) by 0 days.

(21) Appl. No.: 12/675,967

(22) PCT Filed: Aug. 22, 2008

(86) PCT No.: PCT/KR2008/004897
§ 371 (c)(1),
(2), (4) Date: Mar. 1, 2010

(87) PCT Pub. No.: WO2009/028836
PCT Pub. Date: Mar. 5, 2009

(65) Prior Publication Data
US 2010/0256691 A1    Oct. 7, 2010

(30) Foreign Application Priority Data
Aug. 28, 2007   (KR) .................. 10-2007-0086364

(51) Int. Cl.
*A61B 17/04*   (2006.01)
*A61B 17/84*   (2006.01)
(Continued)

(52) U.S. Cl.
CPC .................. *A61B 17/8076* (2013.01)

(58) Field of Classification Search
CPC ............ A61B 17/7047; A61B 17/7049; A61B 17/705; A61B 17/7052; A61B 17/7053;
(Continued)

(56) References Cited

U.S. PATENT DOCUMENTS 5,415,659 A * 5/1995 Lee et al. ............... 606/276
5,439,463 A * 8/1995 Lin ........................ 606/252
(Continued)

FOREIGN PATENT DOCUMENTS

WO   WO2004-028412   4/2004

OTHER PUBLICATIONS

International Search Report mailed Mar. 13, 2009 for PCT/KR2008/004897.

*Primary Examiner* — Si Ming Ku
(74) *Attorney, Agent, or Firm* — STIP Law Group, LLC (57) ABSTRACT

The present invention relates to a fixation device for a correction bar used in the operation of pectus excavatum, and more particularly, to a fixation device for securing the correction bar inserted into a thoracic cavity to a rib in an operation of correcting pectus excavatum, which a sort of thoracic malformation. The fixation device of a correction bar used in the operation of pectus excavatum includes a plurality of rib fixation units fastened to the correction bar and each having a rib support portion and a fastening portion formed at both ends thereof, the rib support portion being formed of a hook portion bent in such a manner as to be hooked and secured to a rib, and the fastening portion being formed of a rectangular through-hole or a slot; and a fastening screw unit adapted to fasten the plurality of rib fixation units hooked and secured to upper and lower ribs to the correction bar through the respective fastening portions of the plurality of rib fixation units.

2 Claims, 7 Drawing Sheets

(51) Int. Cl.
*A61F 2/08* (2006.01)
*A61B 17/80* (2006.01)

(58) Field of Classification Search
CPC ............ A61B 17/7055; A61B 17/7056; A61B 17/8076
USPC ......... 606/246, 300, 330, 324, 75, 326, 328, 606/280–299, 105, 277, 247; 24/458, 24/486, 425, 569; 403/408.1
See application file for complete search history.

(56) References Cited

U.S. PATENT DOCUMENTS

| | | | |
|---|---|---|---|
| 5,667,507 A * | 9/1997 | Corin et al. ................. | 606/250 |
| 5,749,671 A * | 5/1998 | Chauquet ..................... | 403/384 |
| 6,024,759 A | 2/2000 | Nuss et al. | |
| 6,238,396 B1 * | 5/2001 | Lombardo ................. | 606/86 A |
| 6,589,243 B1 * | 7/2003 | Viart et al. ................. | 606/250 |
| 6,669,697 B1 * | 12/2003 | Pisharodi ........... | A61B 17/7007 |
| | | | 606/250 |
| 6,860,884 B2 * | 3/2005 | Shirado et al. ............. | 606/330 |
| 7,156,847 B2 | 1/2007 | Abramson | |
| 2002/0019633 A1 | 2/2002 | Ray | |
| 2003/0109882 A1 | 6/2003 | Shirado et al. | |
| 2004/0117016 A1 | 6/2004 | Abramson | |
| 2005/0267475 A1 * | 12/2005 | Miller, III ...................... | 606/69 |
| 2006/0241591 A1 * | 10/2006 | Biscup et al. ................. | 606/60 |
| 2006/0259141 A1 | 11/2006 | Roman et al. | |

* cited by examiner

FIXATOR FOR BAR OF PECTUS EXCAVATUM REPAIR OPERATION

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

BACKGROUND OF THE INVENTION

Technical Field

The present invention relates to a fixation device for a correction bar used in the operation of pectus excavatum, and more particularly, to a fixation device for securing the correction bar inserted into a thoracic cavity to ribs in an operation of correcting pectus excavatum, which is a sort of chest malformation.

Description of Related Art

Figure 1:
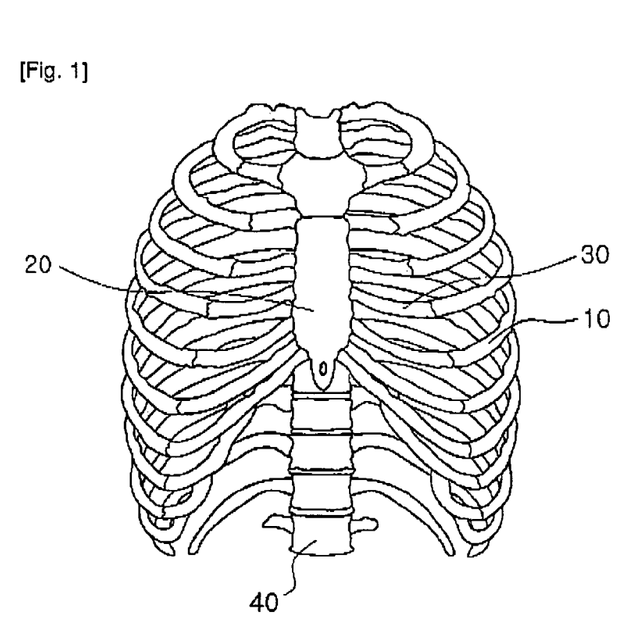
FIG. 1 is a view showing a structure of bones constituting a chest.

A malformation of a chest wall constituting a chest can be largely divided into a pectus excavatum, which is called a depressed chest, and a pectus carinatum, which is called a protruding chest. The causes of such malformation have not been accurately revealed, but it is known that it is caused by genetic factors. As shown in FIG. 1, the bones of the chest are constructed by connecting ribs 10, a sternum 20, costal cartilages 30, and a vertebral column 40, and the pectus excavatum and the pectus carinatum are not caused by malformation of the ribs, but are caused by the abnormality of the costal cartilages 30 constituting a front side of the chest and connecting the sternum 20 to the ribs 10. Such malformation can become severe as people grow, while it was not severe at the time of birth.

Especially, in case of pectus excavatum, the depressed chest walls compress a heart or lungs to bring about malfunction thereof to thereby make the exercise function deteriorated. Furthermore, in case of children, problems are caused in that their respiratory organs become worse or their growing is delayed due to having frequent cold and the repetition of pneumonia, and in addition, they may have emotional and psychological disturbance when they are in childhood, boyhood, and juvenile period.

One of the conventional operation methods for correcting the pectus excavatum is a Lavich operation method, in which the front chest is opened large and almost all of the cartilages are removed. However, the operating method causes problems that the chest walls become weak after the operation, or adhesion is caused to thereby cause the loss of the smooth exercise function of the chest, in addition to forming the big scar on the chest.

In 1997, Donald Nuss who lives in U.S.A. proposes a new operation method (this is called a "Nuss operation method" for correcting the pectus excavatum in place of the conventional Lavich operation method.

Figure 2:
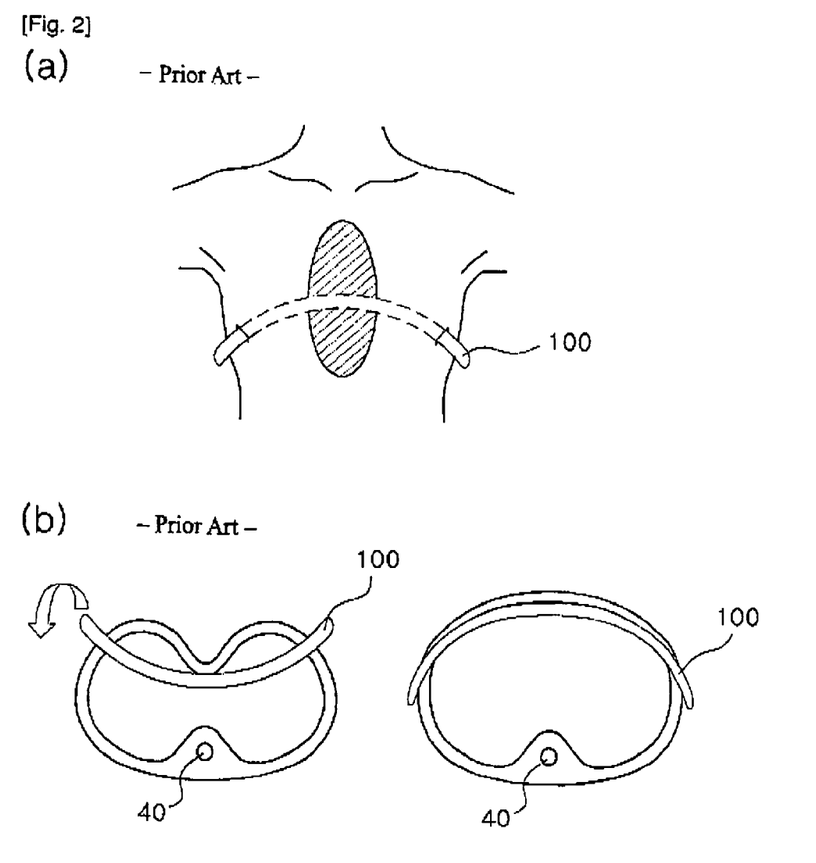
FIGS. 2a and 2b are views showing a principle of a Nuss operation.

As shown by a hatch line in FIG. 2(a), the Nuss operation method is carried out wherein a curved correction bar 100 is inserted after incising a portion under both armpits of a patient with depressed chest walls by about Thus, the Nuss operation method has some advantages in comparison with the Lavich operation method, in that operation trace remains at both sides of the chest by a size of about 1~2 normal chest walls to thereby maintain the flexibility and elasticity of the chest. In addition, the operation time is short and bleeding is little at the time of the operation.

However, the Nuss operation method has a problem that it is not possible to observe the inside of the thoracic wall while the correction bar is being passed through the inside of the thoracic wall so that the operation should be carried out by means of experiences, when the correction bar is pulled out from the opposite side of the chest after it is inserted into the thoracic wall from one side of the chest of the patient. In other words, several cases were reported to cause that the correction bar excessively compressed the internal organs directly affecting the life of a patient, such as a heart or lungs, big vascular tract in the thoracic wall during the passage of the correction bar through the thoracic wall, to damage them or generate bleeding, resulting in the danger of the patient. Also, it was not easy to pull out the correction bar from the opposite side of the chest.

In this regard, a technology disclosed in Korean Patent No. 740193 has been developed to solve such problems arising in the Nuss operation method, which is filed by the same applicant as the present invention.

Moreover, the correction bar can support the thoracic wall to a normal form only when the correction bar is secured to the ribs after lifting the depressed thoracic wall. Conventionally, a sewing thread or a steel wire, and the like are used to bind and secure the correction bar with the surrounding ribs so as to fix the correction bar to the ribs. However, in such a case, a problem occurs in that the supporting force is weakened because the right side and the left side of the correction bar are respectively connected to one rib.

Figure 3:
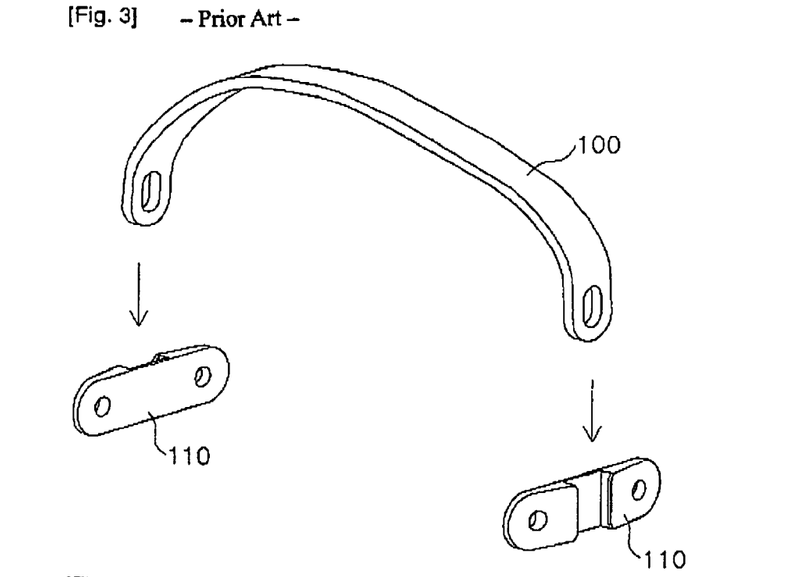
FIG. 3 is a view showing a conventional fixation device.
Figure 4:
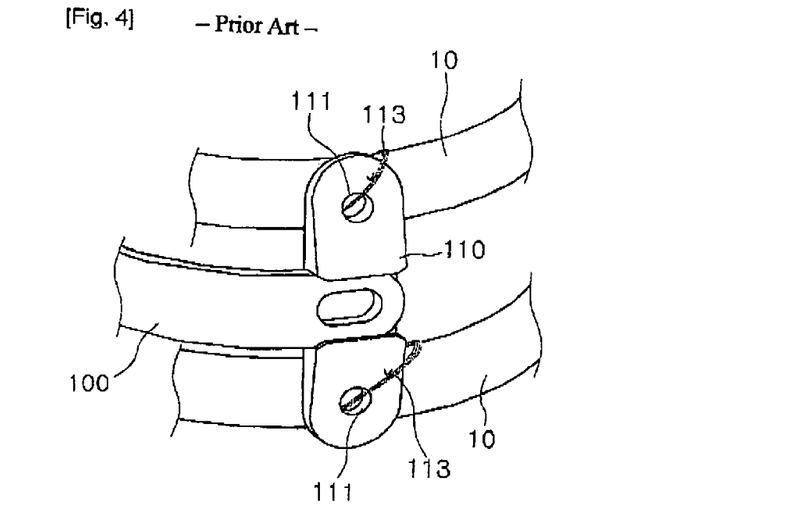
FIG. 4 is a view showing an operation result obtained by using a conventional fixation device.

In this regard, as shown in FIG. 4, after installing a fixation device 110 shown in FIG. 3 at both ends of the correction bar 100, a sewing thread or a steel wire 113 is inserted into a through-hole 111 formed at both sides of the fixation device 110, and then the sewing thread or the steel wire 113 is wound around the surrounding ribs 10 to make a knot to solve such a problem arising in the conventional art.

However, several disadvantages have been caused such that big operation trace remains to thereby rather go off the advantages of the Nuss operation method because the fixation device has no function of self-fixation, and the skin should be more incised up to a portion surrounding the ribs 10 to wind and secure the fixation device around the ribs.

Moreover, there is a possibility of the damage and complication of the organs such as the lungs and the vascular tract by a sewing needle for securing the sewing thread or the steel wire around the ribs. In addition, disadvantages may occur in that fixation fails or re-operation ratio is high.

BRIEF SUMMARY OF THE INVENTION

Technical Problem

Accordingly, the present invention has been devised to solve such conventional problems, and a primary object of the present invention is to provide a fixation device which can secure the correction bar used in the operation of pectus excavatum without excessive incision of skin, thereby improving the beauty effect, and can carry out the fixation of the correction bar, without any sewing on the periphery of ribs.

Also, another object of the present invention is to provide a fixation device which can accurately secure the correction bar to a predetermined position by dispersing load from the correction bar to the surrounding ribs.

Technical Solution

To achieve the above objects, the present invention provides a fixation device of a correction bar used in the repair operation of pectus excavatum and having through-holes bored in a direction of thickness, including a plurality of rib fixation units fastened to the correction bar and each having a rib support portion and a fastening portion formed at both ends thereof the rib support portion being formed of a hook portion bent in such a manner as to be hooked and secured to a rib, and the fastening portion being formed of a rectangular through-hole or a slot; and a fastening screw unit comprising a bottom portion, a fixation portion protruding upward from a top surface of the bottom portion, a skid-preventing means for preventing the fixation portion from skidding when engaged with the through-hole of the correction bar, and a screw formed on a top surface of the fixation portion.

Also, a female screw of the fastening screw unit can be machined on the correction bar.

Advantageous Effects

Therefore, according to the present invention, it is advantageous for cosmetic treatment because the skin can be preferably incised up to a thickness of the correction bar, and the operation can be carried out without any sewing on the periphery of the ribs, and bleeding can be minimized.

In addition, the operation is simple because the load of the correction bar can be dispersed and the correction bar can be accurately secured and removed easily.

BRIEF DESCRIPTION OF THE DRAWINGS

FIGS. 7(a) to 7(f) are views showing several embodiments of a rib fixation unit of the present invention;

FIGS. 9(a) to 9(d) are views showing several forms of the fastening screw unit used in the present invention; and FIG. 10 is an exploded view showing usage of the screw of FIG. 9(b), FIG. 10(a) showing a state before inserting the fastening screw unit into a through-hole of the correction bar, and FIG. 10(b) showing a state after inserting the fastening screw unit into a through-hole of the correction bar.

In the drawings, a reference numeral 10 denotes a rib, a reference numeral 100 denotes a correction bar, and a reference numeral 300 denotes a fastening screw unit.

DETAILED DESCRIPTION OF THE INVENTION

Figure 5:
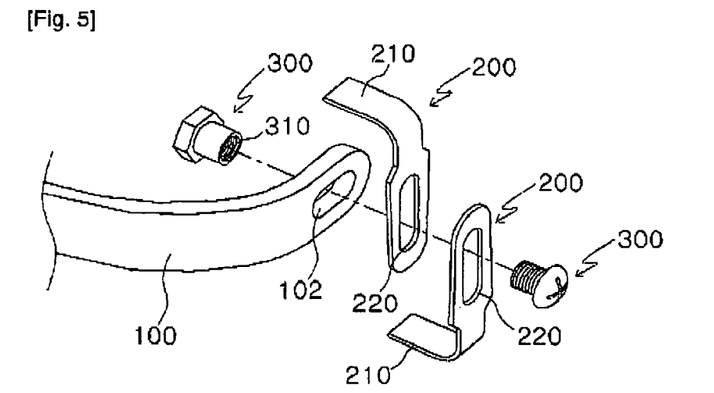
FIG. 5 is an exploded perspective view showing the fixation device of the present invention.

Herein, FIG. 5 is an exploded perspective view showing a fixation device for a correction bar for use in the operation of pectus excavatum according to the present invention.

In the present embodiment, a correction bar 100 is operated generally to be rotated to lift a sinking thoracic wall, after it is inserted into the thoracic wall as shown in FIG. 2(b).

In addition, a rib fixation unit 200 is constructed of a rib support portion 210 formed at one side thereof to support ribs and a fastening portion 220 formed at the other side thereof, and it is inserted into the skin through a portion incised to insert the correction bar.

Figure 6:
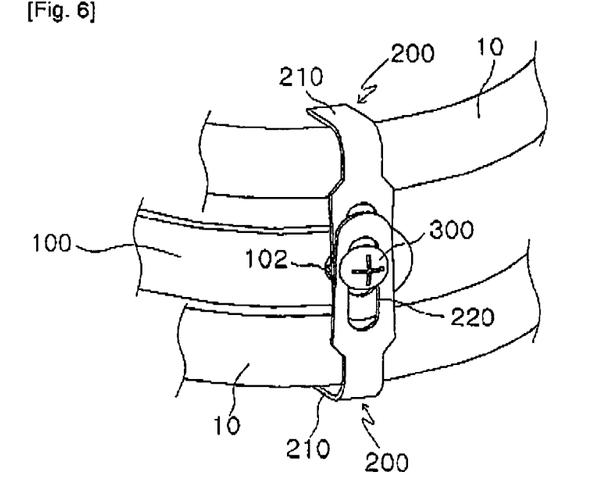
FIG. 6 is a view showing an operation result obtained by using a fixation device of the present invention.

As shown in FIG. 6, the rib fixation unit 200 inserted under the skin, is operated to hook and secure the rib support portion 210 to the rib 10, which is positioned below or above the correction bar 100, and then another rib fixation unit 200 is inserted to make the rib support portion 210 to be hooked and secured to the rib 10, so that the rib fixation unit 200 is secured to the correction bar 100 by means of a fastening screw unit 300 penetrating through the fastening portion 220 of the rib fixation unit 200 formed as a rectangular through-hole and the through-hole 102 formed at the end of the correction bar 100.

Figure 7:
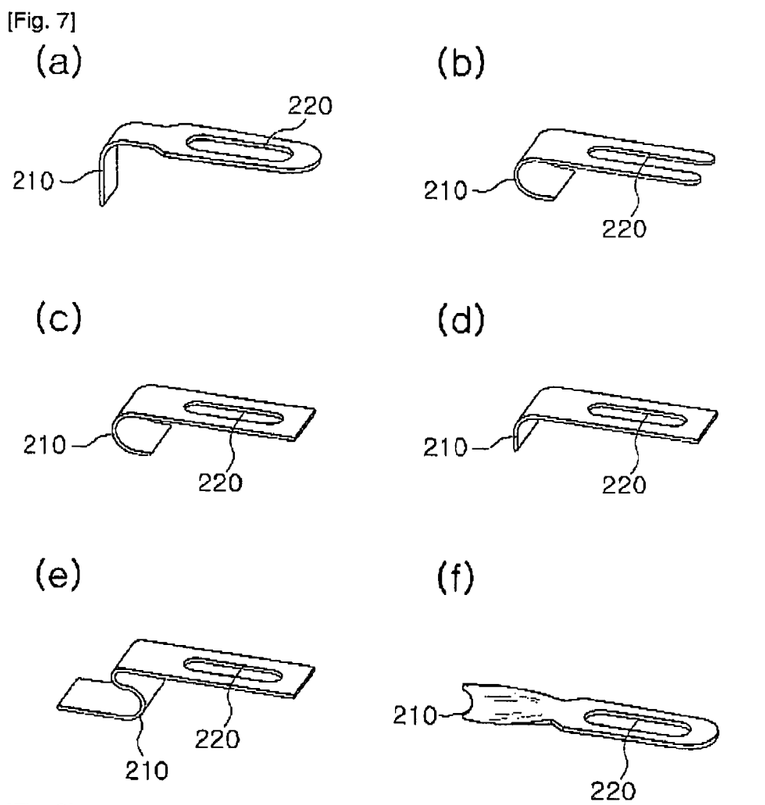

In the present embodiment, although the rib support portion 210 is explained to be provided with a hook portion formed to be bent to a -like shape, as shown in FIGS. 7(a) to 7(f), the rib support portion 210 can be formed to various shapes to support the ribs. In addition, as shown in FIG. 7(f), the rib support portion 210 can be provided with a groove supporting the ribs. Moreover, the rib support portion can be configured to have a variety of shapes, in so far as it can be supported to the ribs without using a separate sewing thread or a steel wire.

Furthermore, the fastening portion is formed at one end of a rib fixation unit, which is opposite to the rib support portion. Also, as shown in FIGS. 7(a) to 7(f), it may be machined as a rectangular through-hole or a slot shape, to facilitate the adjustment of the position of the peripheral ribs and the correction bar by an operator.

Figure 8:
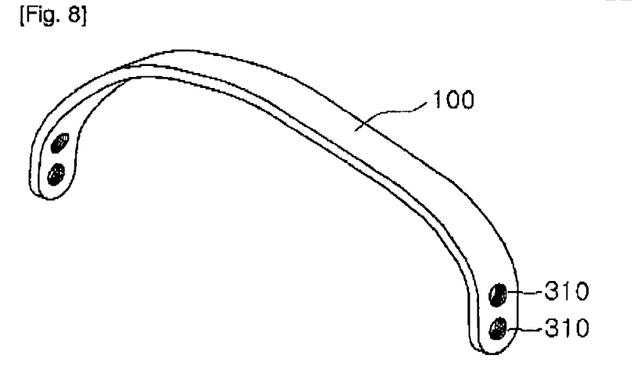
FIG. 8 is a view showing a screw used in the present invention, which is machined on the end of the correction bar.

Moreover, in the present embodiment, while the fastening screw unit is explained to be a separate male screw and a female screw. However, as shown in FIG. 8, it will be possible to form the through-hole of the correction bar 100 to be round and machine the inside thereof to be a female screw 310 so that it can be fastened to a male screw. Also, several through-holes can be provided on the correction bar 100.

The fastening screw unit of the present invention can be machined into various forms as shown in FIGS. 9(a) to 9(d). It is also preferable to provide a fixation portion 320 in various forms, so that it is inserted into the through-hole of the correction bar to fix the position of the correction bar when the screws are fastened to each other.

Figure 9:
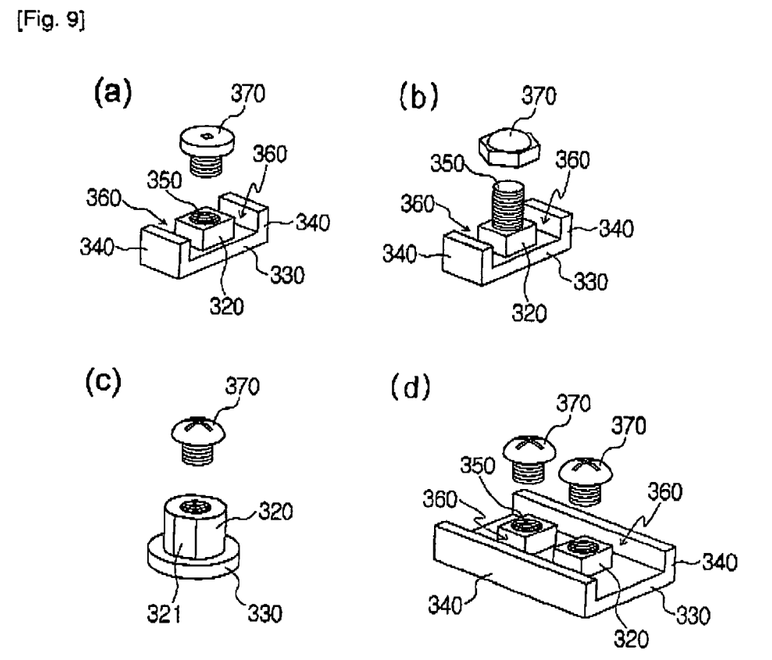

The fastening screw unit as shown in FIG. 9(c) comprises a bottom portion (330), a fixation portion (320) protruding upward from a top surface of the bottom portion (330), a skid-preventing means, comprising a flat portion (321) cut out from a part of a side of the fixation portion (320), for preventing the fixation portion from skidding when engaged with the through-hole of the correction bar, and a screw formed on a top surface of the fixation portion.

The fastening screw unit such as FIG. 9(a), FIG. 9(b), and FIG. 9(d) comprises a rectangular bottom portion (330), a side wall portion (340) extended upward from both ends of the bottom portion (330) and formed, a fixation portion (320) protruding upward from a top surface of the bottom portion (330) between the side wall portions (340), and a screw (350) formed on a top surface of the fixation portion (320).

Figure 10:
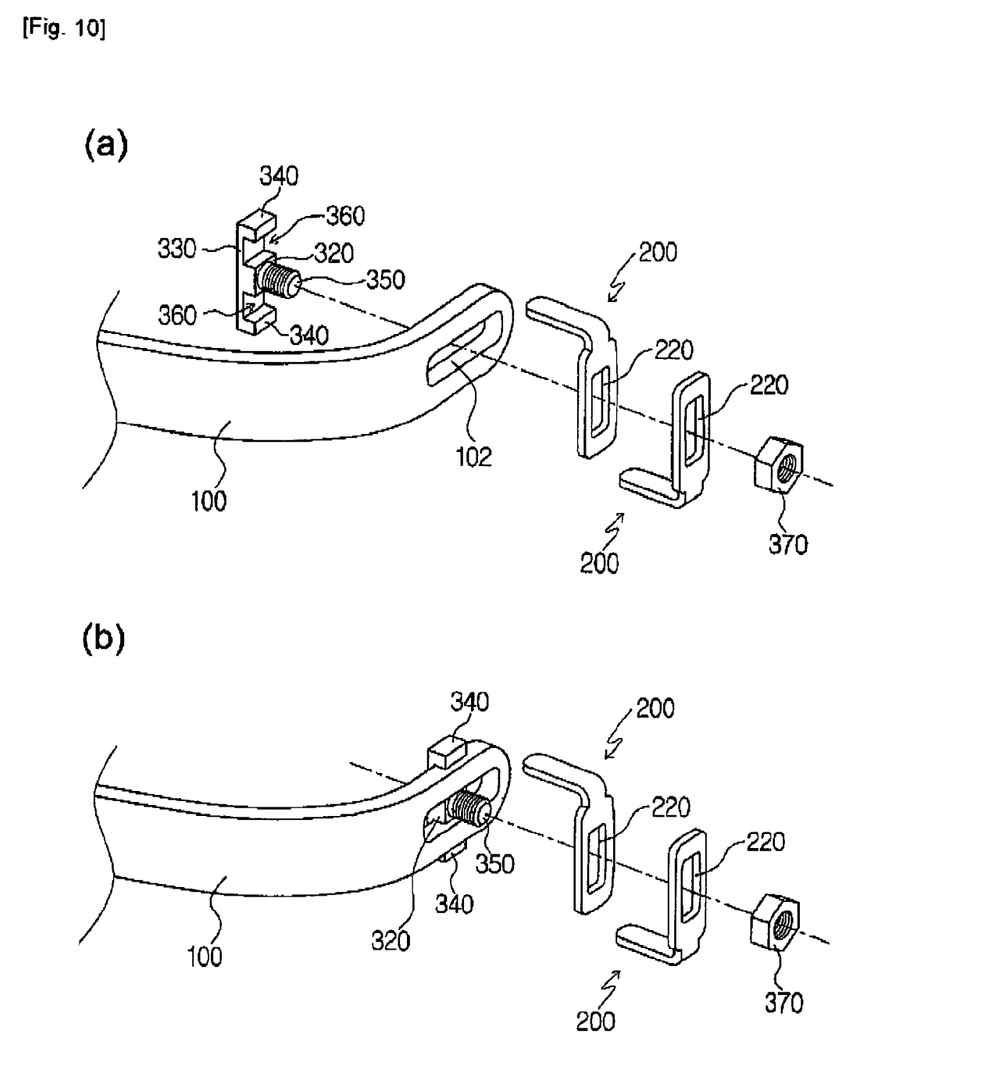

The fastening screw unit shown in FIG. 9(b), as shown in FIG. 10, has the fixation portion (320) inserted through the through-hole (102) of the correction bar (100), and the correction bar (100) is inserted into two concave grooves (360) formed by the side wall portion (340), the bottom portion (330), and the fixation portion (320), and in operation the fastening screw unit would not be disengaged from the correction bar. Since the fastening screw unit engaging the correction bar is fixed without skidding when rotating and engaging the female screw (370) after inserting the fastening portion of the rib fixation unit into the male screw (350), the fixation and engagement are convenient.

INDUSTRIAL APPLICABILITY

As described above, according to the fixation device of the present invention, for fixing the correction bar inserted into the thoracic wall in the operation of correcting the pectus excavatum, which is a type of malformation of the chest, following advantageous effects can be achieved.

It is advantageous for the cosmetic treatment because the skin can be preferably incised to a thickness of the correction bar, and the operation can be carried out without the sewing on the periphery of the ribs, and the bleeding can be minimized.

In addition, the operation is simple because the load of the correction bar can be dispersed and the correction bar can be accurately secured and removed easily.

The invention claimed is:

1. A device for repair operation of pectus excavatum, the device comprising:
    a correction bar having a curved shape along a longitudinal axis, through-holes provided at both longitudinal ends in a direction of a thickness, and having a middle portion for lifting a depressed thoracic wall in the middle portion;
    a plurality of rib fixation units including a first rib fixation unit and a second fixation unit which are fastened to the correction bar, the first rib fixation unit being formed with a first rib support portion and a first fastening portion formed at both ends thereof and the second fixation unit being formed with a second rib support portion and a second fastening portion which are formed respectively at both ends thereof and the first rib support portion and the second rib support portion being formed of a first hook portion and a second hook portion respectively bent in such a manner so as to be hooked fixed and secured to a lower rib or an upper rib, and the first fastening portion and the second fastening portion being formed of a first rectangular through-hole or a first slot and a second rectangular through-hole or a second slot, respectively;
    a fastening screw unit comprising a rectangular bottom portion, a side wall portion extended upward from both ends of the bottom portion, a fixation portion protruding upward from a top surface of the bottom portion between the side wall portions, two concave grooves formed by the side wall portion, the bottom portion, and the fixation portion for preventing the fixation portion from rotating by inserting the correction bar into the two concave grooves, and a screw formed on a top surface of the fixation portion, so as to be inserted through the rectangular through-hole or the slot of the fastening portion and one of the through-holes of the correction bar at the same time;
    wherein the correction bar and the plurality of the rib fixation units are arranged such that the screw is inserted through one of the through-holes of the correction bar, the first rectangular through-hole or the first slot of the first fastening portion and the second through-hole or the second slot of the second fastening portion, and thereby
    the correction bar is placed adjacent to outer surfaces of the upper rib and the lower rib, and a pair of the fastening portions overlap.

2. A device for repair operation of pectus excavatum, comprising:
    a correction bar having a curved shape along a longitudinal axis, through-holes provided at both longitudinal ends in a direction of a thickness, and a middle portion for lifting a depressed thoracic wall in the middle portion, wherein the correction bar is inserted after incising a portion under both armpits of a patient; and
    a plurality of rib fixation units including a first rib fixation unit and a second fixation unit which are fastened to the correction bar, the first rib fixation unit being formed with a first rib support portion and a first fastening portion formed at both ends thereof and the second fixation unit being formed with a second rib support portion and a second fastening portion which are formed respectively at both ends thereof and the first fastening portion and the second fastening portion being formed of a first rectangular through-hole or a first slot and a second rectangular through-hole or a second slot, respectively, wherein the rib fixation unit is inserted into the skin through the portion incised to insert the correction bar and operated to hook and secure the rib support portion to a lower rib, which is positioned below the correction bar, and then another rib fixation unit is inserted to make the rib support portion to be hooked and secured to an upper rib, which is positioned above the correction bar; and
    a fastening screw unit comprising a rectangular bottom portion, a side wall portion extended upward from both ends of the bottom portion, a fixation portion protruding upward from a top surface of the bottom portion between the side wall portions, two concave grooves formed by the side wall portion, the bottom portion, and the fixation portion for preventing the fixation portion from rotating by inserting correction bar into the two concave grooves, and a screw formed on a top surface of the fixation portion, so as to be inserted through the rectangular through-hole or the slot of the fastening portion and one of the through-holes of the correction bar at the same time,
    wherein, the correction bar and the plurality of the rib fixation units are arranged such that the screw is inserted through one of the through-holes of the correction bar, the first rectangular through-hole or the first slot of the first fastening portion and the second through-hole or the second slot of the second fastening portion, and thereby the correction bar is placed adjacent to outer surfaces of upper rib and lower rib, and the first fastening portion and the second fastening portion overlap, and
    wherein the correction bar formed at both ends thereof is supported by the fixation of the upper and lower ribs corresponding to the fastening screw unit and the rib fixation units, and supports the position lifted to a chest wall corresponding to the middle portion of the correction bar through ribs and chest walls.

* * * * *